US 6,699,240 B2

(12) United States Patent
Francischelli

(10) Patent No.: US 6,699,240 B2
(45) Date of Patent: Mar. 2, 2004

(54) METHOD AND APPARATUS FOR TISSUE ABLATION

(75) Inventor: David E. Francischelli, Anoka, MN (US)

(73) Assignee: Medtronic, Inc., Minneapolis, MN (US)

(*) Notice: Subject to any disclaimer, the term of this patent is extended or adjusted under 35 U.S.C. 154(b) by 25 days.

(21) Appl. No.: 10/016,297

(22) Filed: Dec. 12, 2001

(65) Prior Publication Data

US 2003/0073991 A1 Apr. 17, 2003

Related U.S. Application Data

(60) Provisional application No. 60/286,953, filed on Apr. 26, 2001.

(51) Int. Cl.[7] ............................................. A61B 18/04
(52) U.S. Cl. ............................. 606/32; 606/41; 606/50; 606/51; 606/52
(58) Field of Search ........................... 606/32, 41, 50, 606/51, 52; 607/98, 96, 101, 99, 100

(56) References Cited

U.S. PATENT DOCUMENTS

| 5,357,956 A | | 10/1994 | Nardella ................... 128/642 |
| 5,429,131 A | * | 7/1995 | Scheinman et al. ......... 128/642 |
| 5,575,766 A | | 11/1996 | Swartz et al. ................ 604/53 |
| 5,596,995 A | | 1/1997 | Sherman et al. ............ 128/736 |
| 5,685,878 A | | 11/1997 | Falwell et al. ............... 606/49 |
| 5,688,267 A | | 11/1997 | Panescu et al. .............. 606/41 |
| 5,718,701 A | | 2/1998 | Shai et al. .................... 606/41 |
| 5,733,280 A | | 3/1998 | Avitall ......................... 606/23 |
| 5,871,523 A | | 2/1999 | Fleischman et al. ......... 607/99 |
| 5,895,417 A | | 4/1999 | Pomeranz et al. .......... 607/101 |
| 5,906,579 A | * | 5/1999 | Vander Salm et al. ...... 600/424 |
| 5,911,720 A | * | 6/1999 | Bourne et al. ................ 606/41 |
| 6,032,077 A | | 2/2000 | Pomeranz ................... 607/101 |
| 6,045,550 A | | 4/2000 | Simpson et al. .............. 606/42 |
| 6,056,743 A | | 5/2000 | Ellis et al. .................... 606/15 |
| 6,096,037 A | | 8/2000 | Mulier et al. ................. 606/49 |
| 6,133,592 A | | 10/2000 | Kishimoto et al. ......... 257/190 |
| 6,142,944 A | | 11/2000 | Li et al. ...................... 600/453 |
| 6,161,543 A | | 12/2000 | Cox et al. ................... 128/898 |
| 6,237,605 B1 | | 5/2001 | Vaska et al. ................ 128/898 |

FOREIGN PATENT DOCUMENTS

| WO | WO 99/12488 | 3/1999 |
| WO | WO 99/59486 | 11/1999 |
| WO | WO 01/05306 | 1/2001 |
| WO | WO 01/72234 | 10/2001 |
| WO | WO 01/80724 | 11/2001 |

* cited by examiner

Primary Examiner—Roy D. Gibson
Assistant Examiner—Aaron Roane
(74) Attorney, Agent, or Firm—Thomas G. Berry; Daniel W. Latham

(57) ABSTRACT

An ablation system and a method of its use. The system includes a first elongated ablation component carrying a longitudinally extending mechanism for delivery of ablation energy along its length, and a second elongated ablation component movable relative to the first ablation component. The first and second components are provided with a mechanism mounted to and extending along the first and second components for magnetically attracting the first and second components toward one another along the length of the first mechanism for delivery of ablation energy. Preferably, the second elongated ablation component also carries a longitudinally extending mechanism for delivery of ablation energy along its length.

15 Claims, 6 Drawing Sheets

METHOD AND APPARATUS FOR TISSUE ABLATION

This application claims priority from U.S. Provisional Patent Application No. 60/286,953, filed Apr. 26, 2001, incorporated herein by reference in its entirety.

BACKGROUND OF THE INVENTION

The present invention relates to surgical tools and procedures generally and relates more particularly to the use of ablation to treat atrial fibrillation and other disorders.

In patients with chronic atrial fibrillation having tachycardia that resistant to medical treatment, the Maze procedure has been employed. This procedure controls propagation of the depolarization wavefronts in the right and left atria by means of surgical incisions through the walls of the right and left atria. The incisions create blind or dead end conduction pathways, which prevent re-entrant atrial tachycardias from occurring. While the Maze procedure is successful in treating atrial fibrillation, the procedure is quite complex and is currently practiced by only a few very skilled cardiac surgeons in conjunction with other open-heart procedures. The procedure also is quite traumatic to the heart, as in essence the right and left atria are cut into pieces and sewn back together, to define lines of lesion across which the depolarization wavefronts will not propagate.

It has been suggested that procedures similar to the Maze procedure could be instead performed by means of electrosurgical ablation, for example, by applying RF energy to internal or external surfaces of the atria to create lesions across which the depolarization wavefronts will not propagate. Such procedures are disclosed in U.S. Pat. No. 5,895,417, issued to Pomeranz, et al., U.S. Pat. No. 5,575,766, issued to Swartz, et al., U.S. Pat. No. 6,032,077, issued to Pomeranz, U.S. Pat. No. 6,142,944, issued to Swanson, et al. and U.S. Pat. No. 5,871,523, issued to Fleischman, et al, all incorporated herein by reference in their entireties. Hemostat type electrosurgical or cryo-ablation devices for use in performing such procedures are described in U.S. Pat. No. 5,733,280 issued to Avitall, U.S. Pat. No. 6,237,605 issued to Vaska, et al, U.S. Pat. No. 6,161,543, issued to Cox, et al., PCT published Application No. WO99/59486, by Wang and in pending U.S. patent application Ser. No. 09/747,609 filed Dec. 22, 2000 by Hooven, et al., all incorporated herein by reference in their entireties. In order for such procedures to be effective it is desirable that the electrosurgically created lesions are continuous along their length and extend completely through the tissue of the heart. In order for such procedures to be effective it is desirable that the electrosurgically created lesions are continuous along their length and extend completely through the tissue of the heart. Analogous issues arise when attempting to create continuous lines of lesion through the walls of other heart chambers or other organs.

SUMMARY OF THE INVENTION

According to the present invention elongated lesions as might be desired in a maze type procedure or other procedure may be produced using a set of two elongated ablation components carrying means (e.g. an electrode or electrodes) for applying ablation energy (e.g. RF energy) along its length. The ablation components are adapted to be arranged on opposite sides of the walls of the atria or other hollow organs, on either side of the organ walls and to ablate or create lesions in the tissue between the components. The ablation components may also be arranged along opposing external surfaces of an organ, for example opposite sides of an atrial appendage or along opposite sides of the tissue adjacent the bases of the right or left pulmonary veins.

The ablation components are provided with a magnetic system for drawing the components toward one another to compress the wall or walls of an atrium or other hollow organ therebetween, along the length of the components. In these systems, at least one of the components is provided with a magnet or series of magnets extending along the component. The other component is provided with a ferromagnetic member or preferably another magnet or series of magnets extending along its length, having polarity chosen to assure attraction between the two components. The magnet or magnets may be rigid or flexible and may be formed of magnetic material, e.g. rare earth magnets, or may alternatively be electromagnets.

In one preferred embodiment of the invention, the two components comprise opposing jaws of an electrosurgical hemostat, provided with elongated RF electrodes and having straight or curved configurations. In some of these embodiments, the jaws of the hemostat are both rigid and the magnets are present primarily to assure good contact and alignment between the jaws, along their length. In other embodiments, one jaw may be rigid and the other flexible, for example to allow it to be temporarily deformed to access desired locations. In these embodiments, magnetic system also assists the flexible jaw in returning to a configuration corresponding to the rigid jaw, as the jaws are brought into proximity to one another. In some embodiments, one jaw may be shapeable, so that the physician can select a desired configuration, with the other jaw being flexible. In these embodiments, the magnetic system allows the flexible jaw to automatically assume a configuration corresponding to the shapeable jaw. In other embodiments, both jaws might be flexible.

Similar sets of embodiments may be provided wherein the two components are separate from one another, for example mounted to separate handles. Alternatively, a first, external component might be mounted to a handle, to he held by the physician, while a second, internal component may be located on a percutaneously introduced catheter. In these embodiments, the internal component would typically be quite flexible, while the external component would be either rigid or shapeable. In these embodiments the magnetic system allows the internal component to automatically assume a configuration corresponding to the external component, after introduction of the internal component to the interior of the hollow organ.

DESCRIPTION OF THE PREFERRED EMBODIMENTS

Figure 1:
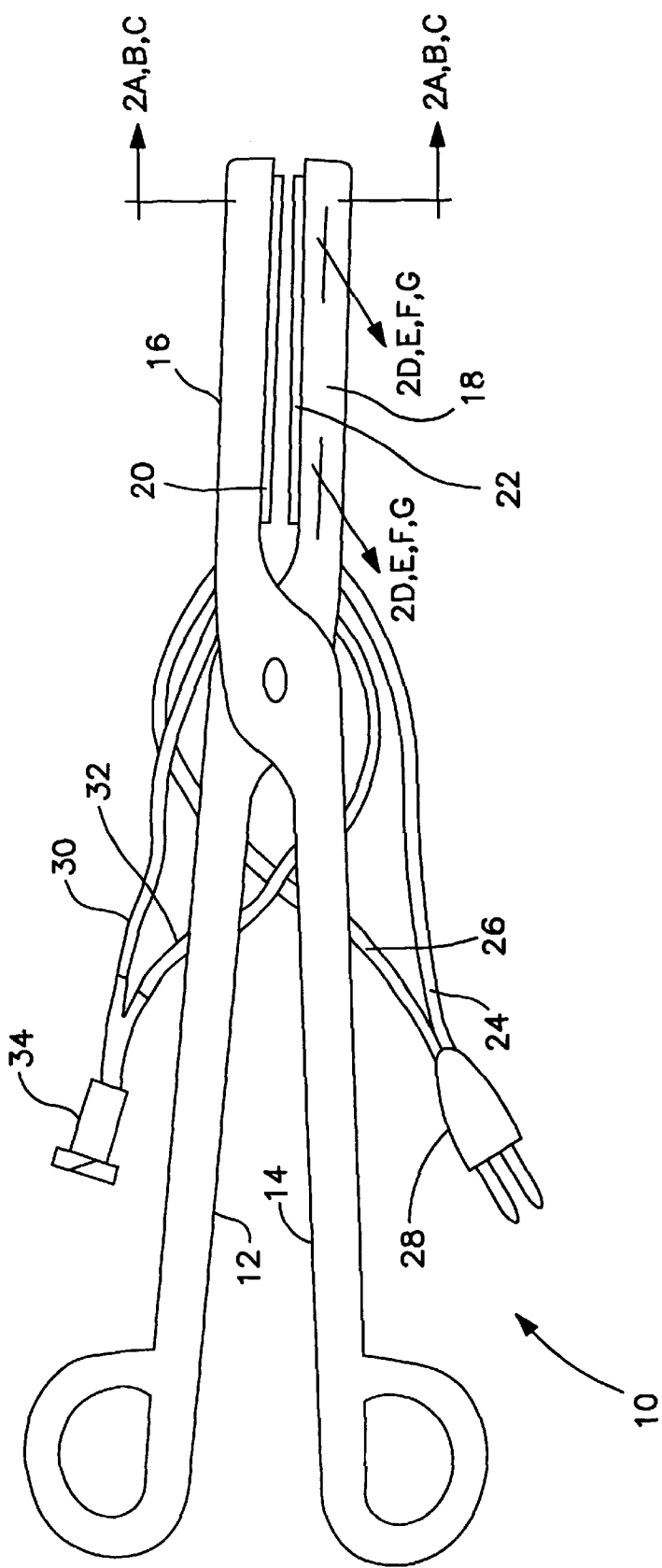
FIG. 1 is a plan view of hemostat of the type in which the present invention may be embodied.

FIG. 1 is a plan view illustrating a bipolar electrosurgical hemostat of a type in which the present invention may usefully be practiced. The hemostat is provided with handles 14 and 12, coupled to pivoting jaws 16 and 18, respectively. Located along jaws 16 an 18 are ablation electrodes 20 and 22, which, as discussed below, take the form of RF electrodes. In alternative embodiments, electrodes 20 and 22 may be employed to apply microwave radiation, or might be replaced by elongated heating or cooling elements to provide for thermal or cryo-ablation along their length. In the embodiment illustrated, the electrodes are irrigated RF electrodes, allowing for delivery of saline or other conductive fluid along their lengths, generally according to the mechanism as described in U.S. Pat. No. 6,096,037 issued to Mulier, incorporated herein by reference in its entirety. Each electrode is provided with a fluid delivery lumen 30, 32, through which the saline or other conductive fluid is delivered to the electrodes. Lumens 30 and 32 are coupled to a luer fitting 34, which may be coupled to a source of conductive fluid. Separate luer fittings for each of lumens 30, 32 might alternatively be provided. Similarly, each electrode is provided with conductors 24, 26 allowing the electrodes to be coupled to a source of ablation energy via electrical connector 28, as noted above. The source of ablation energy may provide RF energy or microwave energy. In alternative embodiments in which electrodes 20 and 22 are replaced by heaters, the fluid delivery lumens may not be provided, and instead, electrical conductors 24 and 26 may be coupled to two elongated resistive heaters arranged along jaws 16 and 18, and coupled to an electrical power source via connector 28. In alternative embodiments in which elongated cooling elements are substituted for electrodes 20 and 22, cooling fluid might be delivered to electrodes via fluid lumens 30 and 32 or alternatively, in the event electrical cooling devices are provided, electrical power might be delivered to the cooling devices via connectors 24 and 26 through electrical connector 28.

While the discussion below focuses on ablation systems in which the particular ablation energy delivered is RF energy, delivered via irrigated electrodes, it should be understood that the present invention can usefully be practiced in conjunction with the other forms of ablation energy referred to above. As such, for purposes of the following discussion, the illustrated and described irrigated RF electrodes should be taken as exemplary of a mechanism for applying ablation energy according to the present invention, rather than as limiting.

Jaws 16 and 18 may have a straight configuration as illustrated, or may be curved. Jaws 16 and 18 are preferably manufactured of a non-ferromagnetic material such a biocompatible plastic, and, as discussed below, carry an elongated magnet or series of magnets, extending along the electrodes 20 and 22, in order to assist in aligning the electrodes relative to one another on opposite sides of tissue to be ablated and to assist in compressing tissue between the electrodes to assure good contact along their length. As described in more detail, jaws 16 and 18 may be rigid, shapeable, or flexible, depending on the particular embodiment of the invention being practiced.

Figure 2A:
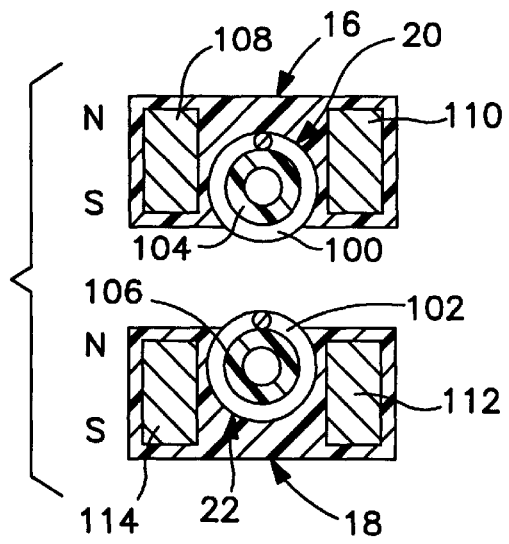
FIGS. 2A through 2G illustrate alternative configurations for the jaws of the hemostat of FIG. 1, illustrating alternative embodiments of the present invention in cross section and longitudinal section.

FIGS. 2A through 2G illustrate various alternative embodiments of the invention, employing different types of magnetic alignment systems and different configurations for the first and second components (in this case the jaws 16 and 18), along which ablation energy is to be applied. FIG. 2A illustrates a cross sectional view through jaws 16 and 18 of the hemostat of FIG. 1, in which the electrodes 20 and 22 take the form of elongated electrode coils 100, 102, respectively, carrying internal porous tubes 104 and 106. Tubes 104 and 106 may be fabricated, for example, of porous polytetrafluoroethylene (PTFE), and have their internal lumens coupled to the fluid lumens 30 and 32 illustrated in FIG. 1. By this mechanism, delivery of conductive fluid such as saline solution along the length of the electrode coils 101 and 102 may be accomplished. While as described, the electrodes 20 and 22 each include a single elongated electrode coil embodiments in which the components (jaws 16 and 18) are provided with multiple electrodes arranged along their length are also within the scope of the present invention.

As illustrated, jaws 16 and 18 are each provided with a pair of magnets or a series of magnets 108, 110, 112, 114, which extend along the jaws 16 and 18. These magnets, shown in cross section, may either be individual elongated magnets or may be a series of shorter magnets, extending along the jaws. The polarities of magnets correspond to the "N" and "S" markings as illustrated, arranged such that the jaws 16 and 18 are attracted to one another along their lengths. Provision of magnets on both sides of the electrodes 18 and 20 assist in assuring that the electrodes will center themselves with respect to one another so that the electrodes will be located directly across from one another when placed on opposite sides of tissue to be ablated. The magnets also assist in compressing the jaws of the hemostat along their length, assuring good contact with the tissue along the length of the jaws.

Jaws 16 and 18 are preferably fabricated of a non-ferromagnetic material, such as a plastic, so that the magnets and electrode coils as illustrated may be insulated from one another. In some embodiments, both jaws 16 and 18 may be rigid and may be pre-formed with the same configuration so that they are parallel to one another. Alternatively, one of jaws 16 and 18 may be rigid, while the other of the two jaws may be quite pliant or flexible, so that upon placement of the jaws on either side of the wall of a hollow organ to be ablated, the magnetic force provided by the magnets causes the flexible jaw to assume a configuration parallel to the rigid jaw and to compress the wall of the hollow organ between the jaws. In additional alternative embodiments, one of the two jaws 16 and 18 may be shapeable by the physician, to assume a desired configuration, with the other of the two jaws being flexible. In this embodiment as well, the flexible jaw is aligned and configured parallel to the shapeable jaw when the two jaws are brought towards one another on either side of the wall of the hollow organ to be ablated. The shapeable jaw may be shapeable by virtue of the material chosen to fabricate the jaw, or means of a shapeable insert, for example, a longitudinally extending rod of nitinol, stainless steel, or other shapeable metal, not illustrated in FIG. 2A.

Figure 2B:
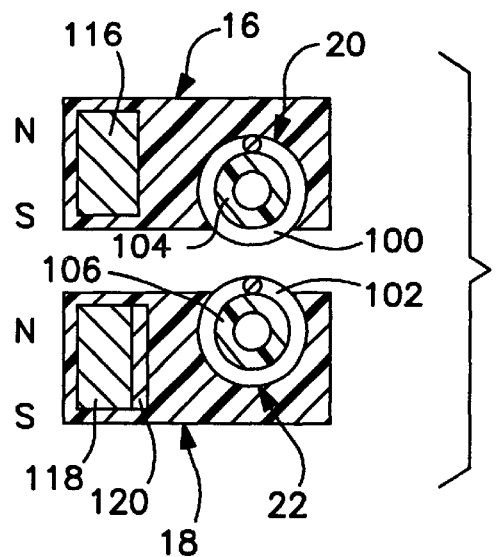

FIG. 2B illustrates an alternative embodiment of an invention according to the present invention, similarly showing a cross section through jaws 16 and 18 of the hemostat of FIG. 1. All elements correspond to identically numbered elements in FIG. 2A. In this embodiment, only a single elongated electrode or line of electrodes 116, 118 is provided for each of the two jaws 16, 18 respectively. This configuration allows for a reduction in the overall size of the jaws, but otherwise functions as described in conjunction with FIG. 2A. In FIG. 2B, an optional metallic shaping wire 120 is shown, mounted adjacent to the magnet or magnets 118, to allow the physician to shape jaw 18. In embodiments in which this shaping wire is present, it is to be expected that jaw 16 would be flexible, and would conform to the configuration provided to jaw 18 by the physician, after placement of the jaws on opposite sides of tissue to be ablated.

Figure 2C:
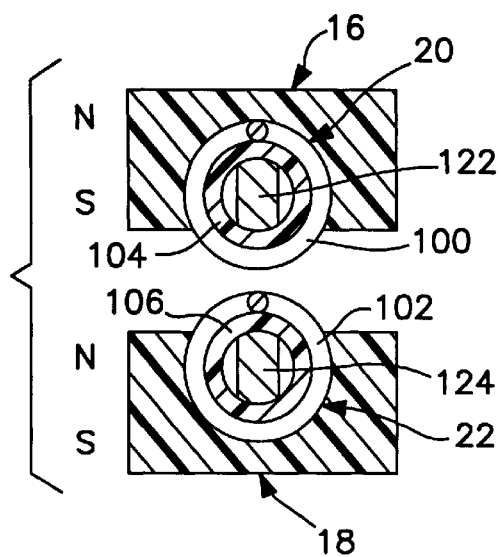

FIG. 2C illustrates a third alternative embodiment of the present invention, also taking the form of a cross section through jaws 16 and 18 of the hemostat of FIG. 1. Identically, numbered components correspond to those illustrated in FIG. 2A. In this embodiment, elongated magnets or series of magnets 122 and 124 are located within the porous fluid lumens 106 and 104, so that magnetic force applied to draw the jaws 16 and 18 toward one another is applied centered with respect to the electrode coils 100 and 102. The various alternative embodiments discussed above in conjunction with FIGS. 2A and 2B may correspondingly be provided in conjunction with the jaws having the general configuration illustrated in FIG. 2C.

As illustrated in 2A, 2B and 2C, the magnets are arranged so that the south pole(s) of the magnet(s) of one jaw are adjacent to the north pole(s) of the magnet(s) of the other jaw. This configuration will be most desirable in conjunction with embodiments in which single, elongated magnets extend essentially along the length of the jaws, and also in embodiments in which a series of shorter, closely spaced magnets extending along the jaws is provided. In embodiments in which magnets extend along the jaw but are more substantially spaced from one another, the polarity of the magnets may be altered, so that along one jaw, the north poles of the magnets may be located at the distal ends of the magnets and the south poles located at the proximal ends wherein on the other jaw, the south poles of the magnets will be located at their distal ends and north poles of the magnets will be located at proximal ends. Alternative magnetic configurations such as this may be employed in any of the embodiments illustrated in FIGS. 2A, 2B and 2C in which the magnets take the form of series of spaced, magnets, running along the lengths of the jaws.

The magnets themselves may be of any appropriate magnetic material. One particularly desirable set of magnetic materials for use in the present invention may be rare earth magnets, due to their extraordinary strength for relatively small sizes and weights. However, elongated flexible magnets might be substituted, as well as ceramic magnets. In addition, as discussed in more detail below, the magnets may be replaced with electromagnetic coils. In further alternative embodiments, it may be possible to employ magnets located in only one of the jaws, substituting a ferromagnetic material such as magnetic stainless steel for the other of the two magnets. For example, in the embodiment illustrated in FIG. 2A, magnets 108 and 110 might be replaced be elongated magnetic stainless steel members. In such an embodiment, the elongated stainless steel members would be attracted to the magnets 112 and 114 as described below and might also be employed to provide the ability to shape the jaw 116 to a desired configuration. Similar substitutions of non-magnetized ferromagnetic materials for the magnets illustrated in FIGS. 2B and 2C are also believed within the scope of the present invention.

Figure 2D:
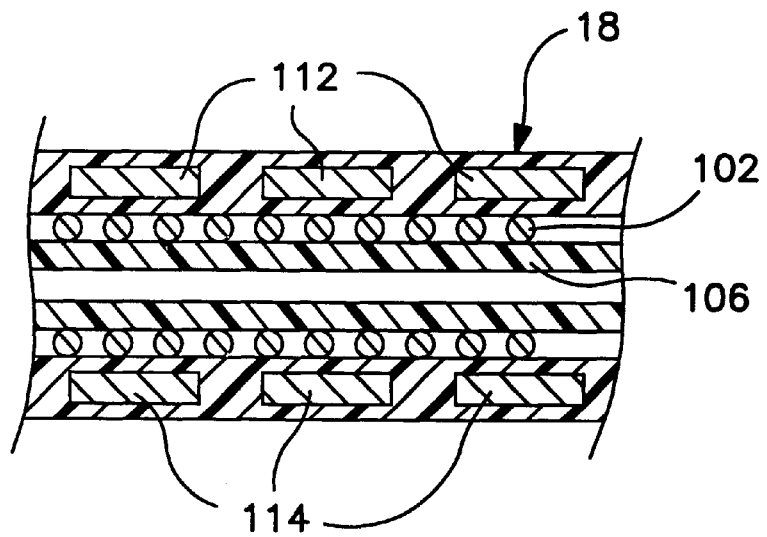

FIG. 2D is a longitudinal sectional view through jaw 18 of the hemostat of FIG. 1. In this embodiment, the magnets 112 and 114 take the form of a series of magnets, mounted within the body of jaw 18. Electrode coil 102 and fluid lumen 106 are also illustrated in longitudinal section.

Figure 2E:
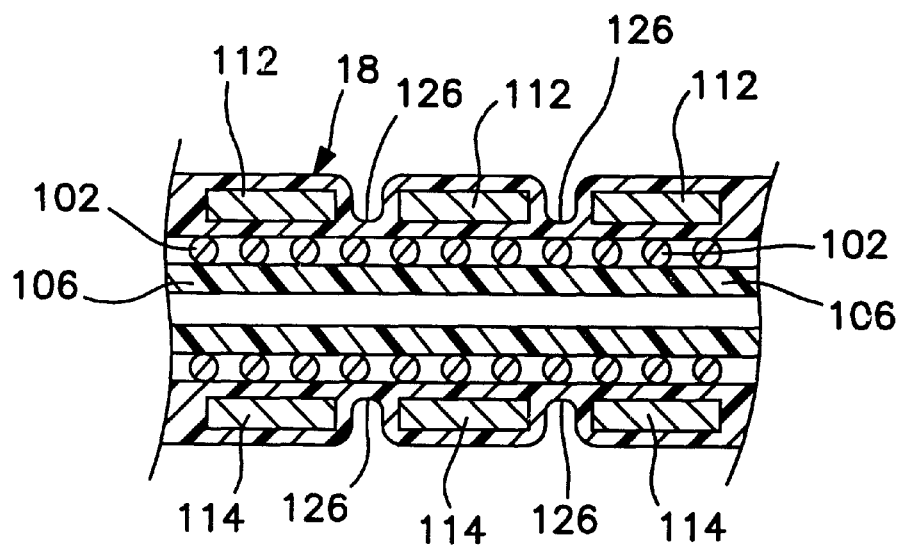

FIG. 2E illustrates an alternative longitudinal sectional view through jaw 18, otherwise as illustrated in FIGS. 1 and 2A. Components corresponds to identically numbered components in FIG. 2A. In this embodiment, however, jaw 18 is provided with indentations 126 in between the individual magnets 114 and 112. These indentations, in conjunction with fabrication of the jaw 18 of the flexible material, define hinge points, facilitating bending of the jaw 18. Such a configuration will be particularly desirable in the event that jaw 16 as illustrated in FIGS. 1 and 2A were to be made rigid or shapeable, with jaw 18 being flexible enough to adapt to the configuration of jaw 16, when placed on the opposite side of tissue to be ablated.

Figure 2F:
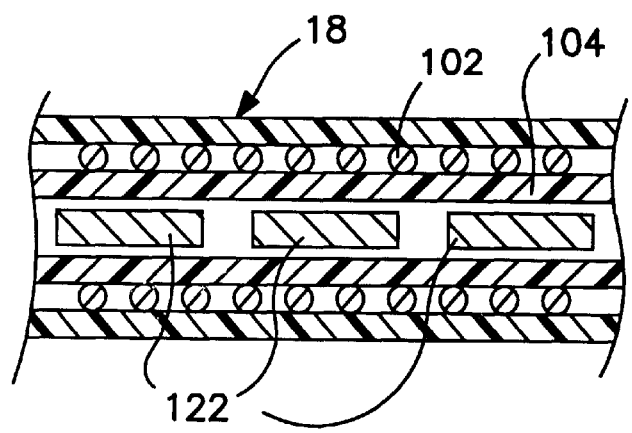

FIG. 2F is a longitudinal sectional view through a hemostat having a jaw configuration as illustrated in FIG. 2C. Components correspond to identically numbered components in FIG. 2C. In this view, the magnet 122 takes the form of a series of magnets located within fluid lumen 104.

Figure 2G:
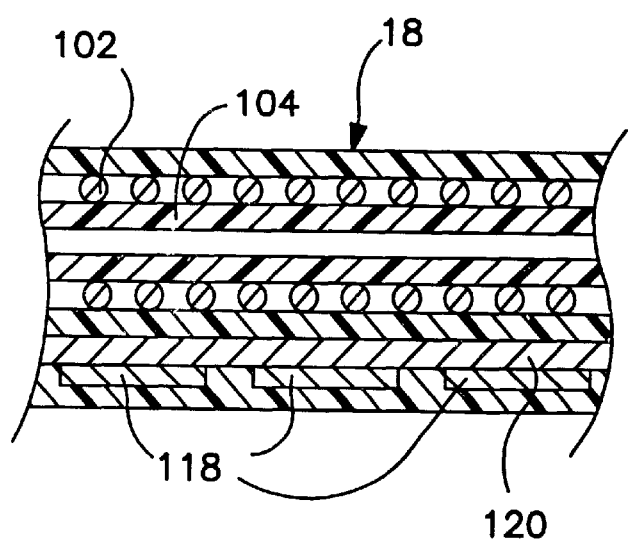

FIG. 2G illustrates a longitudinal section through an embodiment of the present invention having a jaw configuration as illustrated in FIG. 2B. In this embodiment, the magnet 118 take the form a series of magnets 118, located along side the shaping wire 120. Electrode coil 102 and fluid lumen 104 are also visible.

In the embodiments of FIGS. 2D, 2F and 2G, it should be understood that elongated continuous magnets, flexible or rigid might be substituted for a series of individual magnets as illustrated. In addition, it should also be understood that in some embodiments, the magnets as illustrated might be more widely spaced from another, and arranged so that their north/south magnetic access extends longitudinally along the lengths of the jaws, as described above in conjunction with FIGS. 2A through 2C. In such embodiments, the north/south magnetic axes of the magnets in one jaw would be opposite those of the magnets in the other jaw. Jaws employing this arrangement of magnets might also be used in conjunction with a jaw or other ablation component taking the form of a series of electro magnets, for example, coils having their axes extending along the axes of the jaws or other ablation components.

Figure 3:
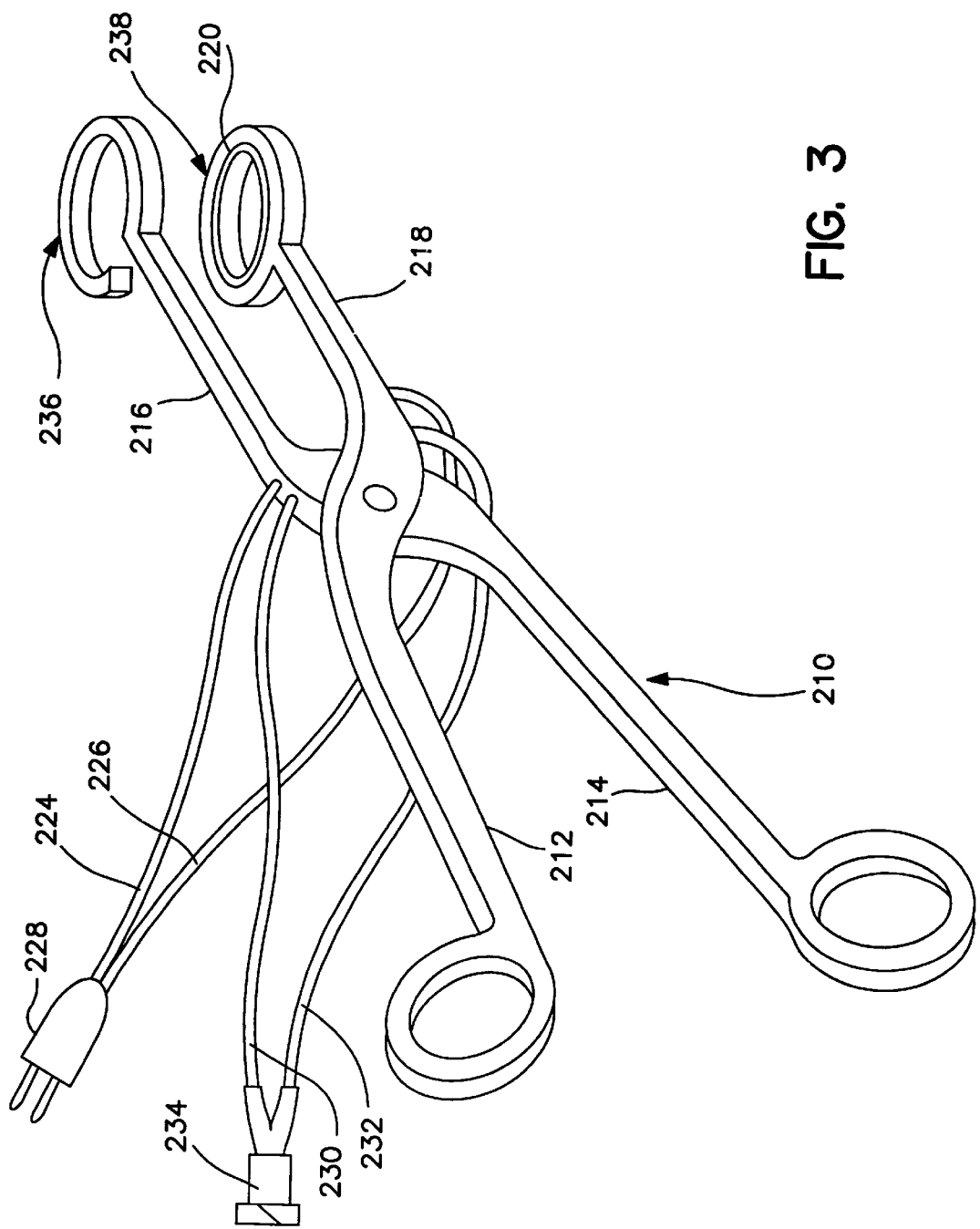
FIG. 3 is a perspective view of a hemostat of a second type, in which the present invention may be usefully practiced.

FIG. 3 is a perspective view of a bipolar electrosurgical hemostat of a second type, appropriate for use in conjunction with the present invention. In this embodiment the hemostat is provided with handles 212 and 214 and elongated jaws 216 and 218. In this case, jaw 218 carries a circular ablation component 238, along which an electrode 220 is arranged. Jaw 216 is provided with a hook shaped ablation component 236, carrying a corresponding electrode facing electrode 220. The instrument of FIG. 3 is particularly adapted for ablations and circling the bases of the pulmonary veins, in the context of an electrosurgical procedure analogous to a maze procedure as discussed above. In this embodiment, it may be desirable that the circular ablation component 238 is either rigid or shapeable by the physician, to allow adaptation of the configuration of the component to this particular anatomy of the patient involved. Component 236 is preferably at least flexible enough to be spread open slightly to facilitate placing of the jaw around the basis of the pulmonary veins and may be quite flexible, relying on the magnetic attraction between components 236 and 238 and to cause component 236 to assume a configuration parallel to component 238. As in conjunction with the hemostat illustrated in FIG. 1, fluid lumens 230 and 232 are provided to allow delivery of a conductive fluid to the electrodes, via luer fitting 234. Electrical conductors 224 and 226 are provided to conduct electrical energy to the electrodes, via electrical connector 228. As discussed above in conjunction with the hemostat of FIG. 1, alternative means for applying ablation energy such as microwave antenna or heaters or coolers to provide thermal or cryo-ablation may be substituted for the electrodes.

Figure 4:
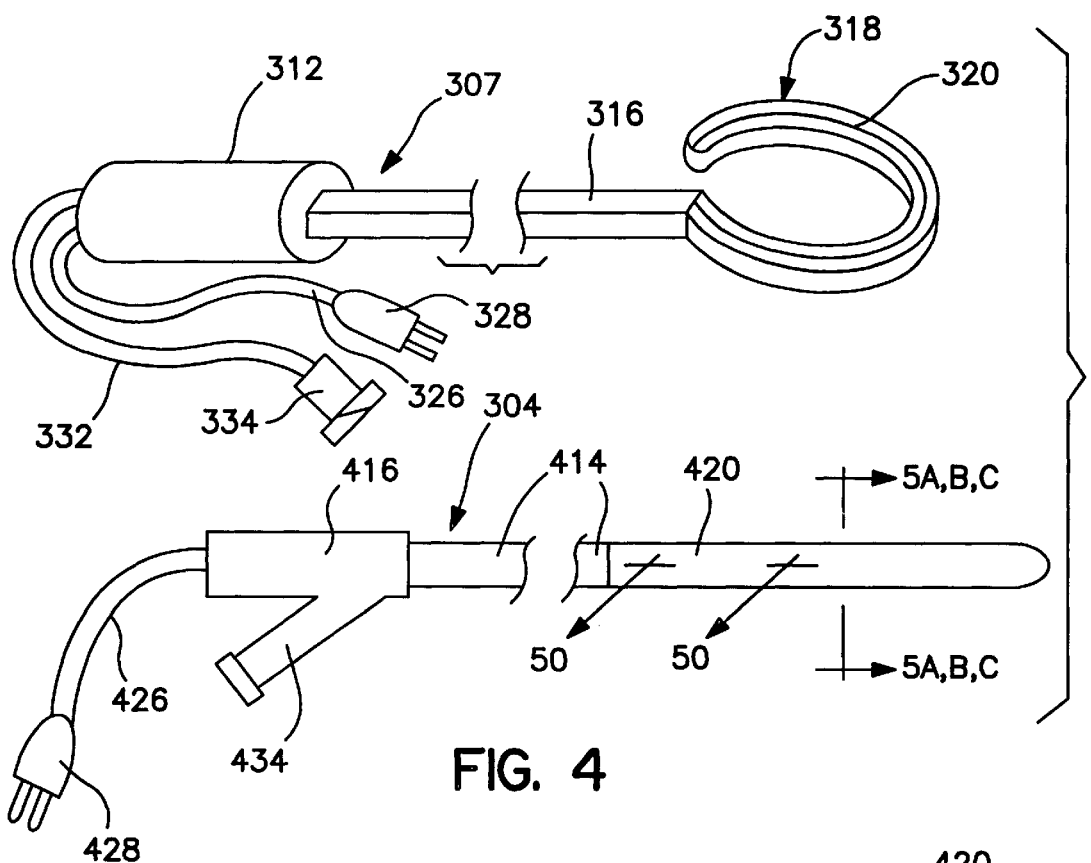
FIG. 4 is an illustration of a system employing the invention, including a first external component and a separate second internal component.

FIG. 4 illustrates an additional alternative embodiment of the invention, in which the two ablation components are separate from one another rather than being joined as in the hemostats of FIGS. 1A and 3. In this embodiment, the first component corresponds generally to jaw 216 of the hemostat of FIG. 3, provided in this case with a handle 312 allowing the physician to manipulate the device. An electrode 320 extends around the curved ablation component 318, and may be, as discussed above, an irrigated electrosurgical electrode, provided with fluid via lumen 332 and luer fitting 334 and provided with electrical power via conductors 326 and electrical connector 328. In use, the curved ablation component 318 will be placed on the exterior surface of the organ to be ablated, for example, placed around the bases of a patient's pulmonary veins. In this particular embodiment, the curved ablation component 318 is preferably rigid or malleable, as the internal ablation component 304, as discussed below, will be quite flexible.

The internal ablation component 304 takes the form of a catheter having an elongated catheter body 414 carrying an electrode along its distal portion 420. Distal portion 420 may have a structure corresponding generally to the illustrated structures for the jaws of the hemostats as illustrated in FIGS. 2A through 2G, with the caveat that the structure of a distal portion 420 of the catheter should be fabricated of a sufficiently flexible material that it may be introduced percutaneously and navigated to the desired location within the organ to be ablated. For example, the catheter might be advanced through the vascular system to the interior of the left atrium, to a position adjacent the openings into the pulmonary veins. Alternatively, as illustrated in FIGS. 5A through D below, the distal portion 420 of the catheter may be specifically optimized for location at the distal portion of a catheter. As illustrated, the proximal end of the catheter is provided with a fitting 416 carrying a fluid coupling 434 allowing delivery of saline or other conductive fluid to the electrode located along the distal portion 420 of the catheter. Electrical power is provided to the electrode by means of conductors 426 and connector 428 in a fashion analogous to that described above for the other embodiments.

FIGS. 5A–5D illustrate various alternative configurations for the distal portion 4120 of the catheter 304 illustrated in FIG. 4. The embodiments of the invention as illustrated in FIGS. 5A–5D may also be employed in external ablation components as illustrated in FIG. 4 or in hemostat type devices as illustrated in FIGS. 1 and 3.

Figure 5A:
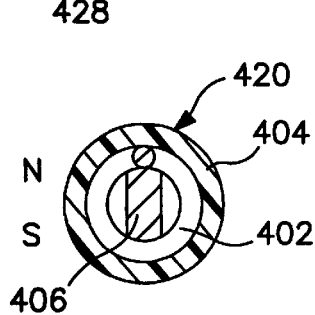
FIGS. 5A through 5D illustrate alternative embodiments of the distal portion of the internal component illustrated in FIG. 4, in cross section and longitudinal section.

FIG. 5A is cross sectional view through the distal portion 420 of the catheter illustrated in FIG. 4, showing a first embodiment of invention particularly optimized for use as part of a percutaneously introduced catheter. In this embodiment, the outer surface of the distal portion comprises a porous tube 404, which may be made of PTFE as discussed above, surrounding an electrode coil 402. A magnet or series of magnets 406 is mounted within the lumen of the electrode coil 402. In this embodiment, fluid is delivered through the lumen of the electrode coil 402, permeates through the porous wall of tube 404, and electrical energy provided by electrode 402 is coupled to the tissue to be ablated via the conductive fluid in the wall and on the surface of tube 404. As illustrated, the electrode is shown having its magnetic polarity such that its north/south axis runs transverse to the axis of the catheter. However, alternative embodiments employing a series of spaced magnets having their north/south axis running along the axis of the catheter are also within the scope of the invention.

Figure 5B:
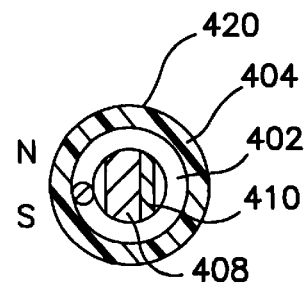

FIG. 5B shows an alternative cross section through the distal portion 420 of the catheter FIG. 4. Numbered elements correspond to identically numbered elements in FIG. 5A. In this embodiment, however, a shaping wire 410 is shown, allowing the physician to provide a desired configuration to the distal portion 420 of the catheter. For example, the catheter may be biased to assume a generally circular configuration, which is straightened during the passage of the catheter through the vascular system, with shaping wire 410 allowing it to resume its desired configuration when no longer retrained by vascular system.

Figure 5C:
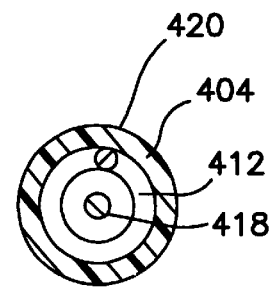

FIG. 5C shows an additional alternative cross section through the distal portion 420 of the catheter FIG. 4. Numbered elements correspond to identically numbered elements in FIG. 5A. In this embodiment, coil 412, however is not an ablation electrode but instead is employed as an electromagnet to attract the catheter to an associated external ablation component. Delivery of ablation energy, e.g. RF or microwave, is accomplished by central wire 418.

Figure 5D:
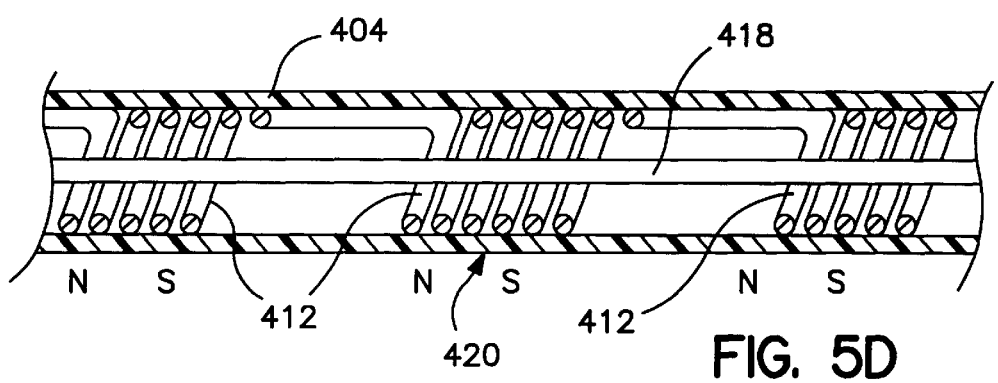

FIG. 5D shows a longitudinal sectional view through the distal portion 420 of a catheter having a cross section as illustrated in FIG. 5C. Numbered elements correspond to identically numbered elements in FIG. 5C. In this view it can be seen that coil 412 is one of a series of spaced electromagnet coils spaced along the distal portion 420 of the catheter. As illustrated, coils 412 are wired in series, however, in alternative embodiments they may be wired for individual activation.

In conjunction with the above disclosure, I claim:

1. An ablation system, comprising:
   a first elongated ablation component carrying a longitudinally extending first means for delivery of ablation energy;
   a second elongated ablation component and movable relative to the first ablation component; and
   means mounted to and extending along the first and second components for magnetically attracting the first and second ablation components toward one another along the length of the first means for delivery of ablation energy wherein the first component is manually shapeable and the second component is sufficiently flexible to be deflected into alignment with the first component by the attracting means.

2. A system as in claim 1 wherein the second elongated ablation component carries a longitudinally extending second means for delivery of ablation energy.

3. A system as in claim 1 or claim 2 wherein the attracting means comprises a magnet mounted to one of the first and second components.

4. A system as in claim 3 wherein the magnet comprises a rare earth magnet.

5. A system as in claim 3 wherein the magnet comprises an electromagnet.

6. A system as in claim 1 or claim 2 wherein the attracting means comprises magnets mounted to both of the first and second components.

7. A system as in claim 1 or claim 2 wherein the first and second components are rigid.

8. A system as in claim 1 or claim 2 wherein the first component is rigid and the second component is sufficiently flexible to be deflected into alignment with the first component by the attracting means.

9. A system as in claim 1 or claim 2 wherein the first and second components are mounted to one another.

10. A system as in claim 9 wherein the first and second components are mounted to one another by means of a hinge.

11. A system as in claim 9 wherein the first and second components are mounted to jaws of an electrosurgical hemostat.

12. A system as in claim 1 or claim 2 wherein the first and second components are not mounted to one another.

13. A system as in claim 12 wherein one of the first and second components is a catheter.

14. A system as in claim 1 or claim 2 wherein one of the first and second components are provided with a pre-formed curve.

15. A system as in claim 1 or claim 2 wherein both of the first and second components are provided with pre-formed curves.

* * * * *